United States Patent
Topel et al.

(10) Patent No.: US 6,468,228 B1
(45) Date of Patent: Oct. 22, 2002

(54) SURGICAL TISSUE MORCELLATOR

(75) Inventors: Howard C. Topel, Deerfield, IL (US); Thomas L. Foster, Poland, IN (US)

(73) Assignee: Vance Products Incorporated, Spencer, IN (US)

( * ) Notice: Subject to any disclaimer, the term of this patent is extended or adjusted under 35 U.S.C. 154(b) by 811 days.

(21) Appl. No.: 08/666,661

(22) Filed: Jun. 18, 1996

(51) Int. Cl.$^7$ .................. A61B 10/00; A61M 25/00
(52) U.S. Cl. .................. 600/567; 604/264; 606/167; 600/564
(58) Field of Search .................. 600/562, 566; 604/264; 606/184, 185, 190

(56) References Cited

U.S. PATENT DOCUMENTS

| | | | |
|---|---|---|---|
| 1,888,347 A | | 11/1932 | Diamond .................. 30/361 |
| 2,850,007 A | * | 9/1958 | Lingley .................. 128/754 |
| 3,995,619 A | | 12/1976 | Glatzer .................. 128/2 B |
| 4,010,543 A | | 3/1977 | Nusbaum .................. 30/113.1 |
| 4,010,737 A | | 3/1977 | Vilaghy et al. .......... 128/754 |
| 4,043,323 A | | 8/1977 | Komiya .................. 128/4 |
| 4,257,429 A | | 3/1981 | Dickhudt et al. ........ 128/786 |
| 4,682,606 A | | 7/1987 | DeCaprio .................. 128/754 |
| 5,018,530 A | | 5/1991 | Rank et al. .............. 128/754 |
| 5,279,610 A | * | 1/1994 | Park et al. ............ 128/200.26 |
| 5,314,417 A | * | 5/1994 | Stephens et al. ......... 604/264 |
| 5,382,255 A | | 1/1995 | Castro et al. ............ 606/143 |
| 5,399,167 A | * | 3/1995 | Deniega .................. 604/264 |
| 5,439,474 A | * | 8/1995 | Li .................. 128/754 |
| 5,488,958 A | | 2/1996 | Topel et al. .............. 128/754 |
| 5,546,937 A | * | 8/1996 | Stuart et al. ......... 128/207.15 |
| 5,626,596 A | * | 5/1997 | DeSatnick et al. ....... 128/754 |
| 5,709,671 A | * | 1/1998 | Stephens et al. ......... 604/264 |

FOREIGN PATENT DOCUMENTS

WO  9212676  8/1992  .......... A61B/17/32

OTHER PUBLICATIONS

Semm, K., "Pelviscopy–Operative Guidelines," 1988.

Nordenström, Björn, "New Instruments for Biopsy", Radiology, vol. 117, pp 474–475, Nov. 1975.

* cited by examiner

Primary Examiner—John G. Weiss
(74) Attorney, Agent, or Firm—James B. Hunt

(57) ABSTRACT

A surgical tissue morcellator (10) for percutaneously morcellating and debulking tissue during a minimally invasive, endoscopic surgical procedure. In an insertion configuration, the morcellator includes an outer cutting sheath (11) and an insertion member (15) inserted therethrough and positioned relative thereto via a connector (20). The connector includes an adaptor (18) positioned at the proximal portion (13) of the outer cutting sheath. The adaptor includes a lock member (22) such as a pin extending radially into the bore (19) of the adaptor. A second lock member (23) in the form of a T-shaped slot is formed in the surface of the insertion member to receive and position the pin therein. In a morcellation configuration, the morcellator includes a handle (24) that is positioned in the bore of the adaptor. A tissue fixation member (26) is inserted through the handle and outer sheath passages (25, 14) and includes a distal portion (27) with a helical coil (29) that extends from the distal cutting end (12) of the outer cutting sheath for affixation to a tissue mass (50). The tissue fixation member also includes a plurality (44) of helical grooves (30) of which a plurality (45) of projections (32) extend from the handle and into the grooves. These projections are positioned on the ends of a plurality (49) of rocker arms (33) which are pivotally mounted in the wall (37) of the handle. The engagement projections are extended selectively into and out of the passage of the handle via a retainer ring (43) that longitudinally slides on the neck portion (65) of the handle.

20 Claims, 8 Drawing Sheets

SURGICAL TISSUE MORCELLATOR

TECHNICAL FIELD

This invention relates generally to surgical instruments and particularly to a surgical tissue morcellator for use in minimally invasive, surgical procedures.

BACKGROUND OF THE INVENTION

Undesirable tissue masses such as fibroid tumors are typically dense, tough, and bulky. These characteristics make it difficult to remove a relatively large and dense tumor using the instruments commonly employed in minimally invasive endoscopic surgery. Endoscopic tissue graspers and cutters have jaws of limited size and inadequate closing force. Therefore, fibroid tumors are commonly removed by open surgery, which permits direct manipulation and cutting. As a result of the open surgical procedure, the patient experiences a long hospital stay and a long healing and recovery period of typically six to eight weeks along with a greater risk of infection and a larger area of scaring.

One minimally invasive surgical procedure involves the use of a surgical cutting instrument for coring tissue affixed thereto. This instrument was developed by the present inventors and is fully described in U.S. Pat. No. 5,488,958. This surgical cutting instrument involves the use of an outer sheath with a distal cutting end that is inserted through a surgical access sheath. The cutting instrument includes an inner member that is inserted through the outer cutting sheath and affixed to the fibroid tissue mass. The outer cutting sheath is then advanced into the tissue mass for coring the affixed tissue. The inner member is again affixed to another portion of the tissue mass, and the coring procedure repeated. This procedure is continued until the fibroid tissue mass is debulked and easily removed through the surgical access sheath. Although well suited for its intended purpose, the surgical cutting instrument is limited in size to the diameter of the surgical access sheath, which is commonly 10 mm in diameter. Furthermore, physicians have requested refinement of the engagement assembly that is positioned at the proximal end of the outer sheath for advancing the outer sheath with respect to the inner member. This refinement was requested to lessen the amount of torque required to core extremely dense fibroid tissue masses. In addition, the engagement assembly also experienced lateral slippage when extremely tough fibroid tissue masses were encountered.

SUMMARY OF THE INVENTION

The foregoing problems are solved and a technical advance is achieved in an illustrative surgical tissue morcellator for percutaneously morcellating and debulking tissue during a minimally invasive, endoscopic surgical procedure. The morcellator preferably comprises an outer cutting sheath having a distal cutting end and an insertion member having a distal portion which can be inserted through a passage of the sheath. The distal portion of the insertion member includes a distal end that is atraumatic to tissue and extendable from the distal cutting end of the outer sheath. A connector is disposed on the outer sheath and/or the insertion member and is configured to position the insertion member relative to the outer sheath. During direct insertion into a percutaneous access site, this surgical tissue morcellator advantageously dilates the access site atraumatically and morcellates cores of tissue without being limited to the diameter of introducer sheaths.

The connector includes an adaptor connected to the proximal portion of the outer sheath and is configured to join the proximal sheath portion and the proximal portion of the insertion member. The adaptor includes a bore that communicates with the sheath passage and is configured to receive the proximal portion of the insertion member therein.

To fixedly position the outer sheath and the insertion member relative to each other, the connector advantageously includes a first lock member such as a pin extending into the adaptor bore. The proximal portion of the insertion member includes a second lock member such as a T-shaped slot disposed therein to receive the lock member pin.

To fix the relative position of the tissue mass during the percutaneous morcellating procedure, the insertion member of the morcellator is removed from the outer sheath, and a handle is positioned relative to the outer sheath via the connector. The handle includes a passage extending longitudinally therethrough which communicates with the sheath passage when the handle is positioned relative to the outer sheath. The morcellator further includes a tissue fixation member which is inserted through the sheath and handle passages and has at least a portion that can be extended from the distal cutting end of the sheath. The distal end of the tissue fixation member has a part such as a helical coil or corkscrew that is fixable in tissue.

To advantageously control rotational and longitudinal movement of the outer sheath with respect to the tissue fixation member, the tissue fixation member includes a helical groove in an external surface thereof, and the handle includes a projection that selectively extends into the handle passage and helical groove when the helical groove is positioned in the handle passage. To circumferentially distribute torque applied thereto, the tissue fixation member advantageously includes a plurality of helical grooves such as a five start external thread. Correspondingly, the handle also includes a plurality of projections that selectively extend into the plurality of helical grooves.

To selectively position a projection into a helical groove, the handle includes a rocker arm that extends between an external surface thereof and the handle passage. The projection is positioned about a rocker arm end that is extendable into the handle passage. One or more of these rocker arms are each pivotally mounted in a slot that extends through a wall of the handle. Each projection is mounted on the internal side of the rocker arm at the rocker arm end. Second and third projections are positioned on the external side and at opposite ends of each rocker arm. The handle further advantageously includes a retainer ring that selectively moves longitudinally along the handle to engage the second and third projections on the external side of each rocker arm to position selectively the first projection in a helical groove of the tissue fixation member.

In another configuration, the surgical tissue morcellator comprises the outer cutting sheath with the handle removably connected to the proximal sheath portion. The handle includes one or more slots extending through a wall thereof with a rocker arm pivotally mounted therein. A projection is positioned as previously described on the internal side of each rocker arm. The handle advantageously includes a retainer ring disposed about each rocker arm and movable to engage selectively opposite ends of the rocker arm on the external side thereof. As a result, longitudinal and rotational movement of the outer sheath causes the distal cutting end to rotate and core tissue affixed to a tissue fixation member that is positioned in the handle and sheath passages and engaging the first projection on each rocker arm end.

The morcellator further comprises an adaptor that is disposed on the proximal portion of the outer cutting sheath. The adaptor includes a bore communicating with the handle and sheath passages, the handle being configured for positioning in the bore of the adaptor. The adaptor includes a lock member such as a pin extending into the adaptor bore, and the handle includes another lock member such as a T-shaped slot disposed on the external surface thereof to receive the lock member pin. A tissue fixation member is inserted through the sheath and handle passages and has a distal fixation end which can be extended from the distal cutting end of the outer sheath to affix tissue thereto.

DETAILED DESCRIPTION

Figure 1:
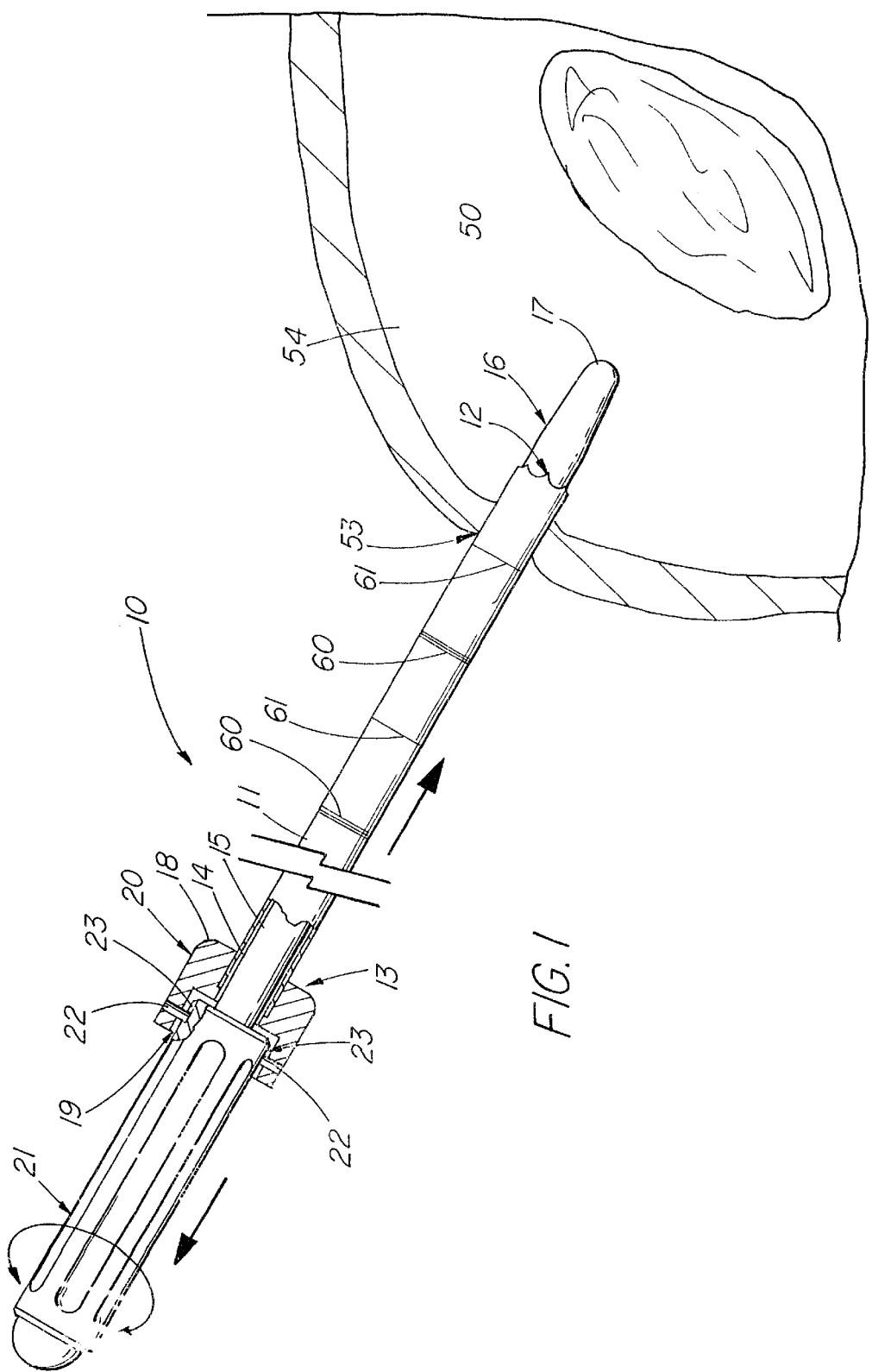
FIG. 1 depicts a partially sectioned side view of a preferred surgical tissue morcellator of the present invention in an insertion configuration and being percutaneously introduced into a body cavity of a patient.

FIG. 1 depicts a partially sectioned side view of a preferred embodiment of surgical tissue morcellator 10 in an insertion configuration and being percutaneously inserted through surgical access site 53 into body cavity 54 of a patient for morcellating fibroid tissue mass 50 during a minimally invasive, endoscopic surgical procedure. Surgical access site 53 is formed using, for example, a commercially available trocar introducer sheath having a typical 10 mm inside diameter. The trocar introducer sheath is removed, and the surgical tissue morcellator is inserted through the access site with insertion member 15 positioned in passage 14 of outer cutting sheath 11 of the morcellator. As depicted, distal portion 16 of the insertion member includes blunt, distal insertion end 17 that is atraumatic to tissue and extends beyond distal cutting end 12 of the outer sheath. The blunt, tapered end of the insertion member and outer sheath dilate access site 53 to a larger diameter of, for example, 15 mm, which corresponds to the outer diameter of outer cutting sheath 11 of the morcellator.

In the insertion configuration, surgical tissue morcellator 10 includes outer cutting sheath 11, insertion member 15 that is inserted through sheath passage 14, and connector 20 that is disposed on, for example, proximal sheath portion 13. In a morcellating configuration of the morcellator, the insertion member is removed from the outer cutting sheath; and handle 24 (FIG. 3) is joined with connector 20. Tissue fixation member 26 (FIG. 4) is positioned in outer cutting sheath 11 and extended from distal cutting end 12 in readiness for tissue morcellation.

Connector 20 is configured to position the insertion member relative to the outer sheath and, in particular, to fixedly position the insertion member longitudinally in passage 14 of outer sheath 11. Connector 20 includes adaptor hub 18 that is positioned on proximal sheath portion 13 of outer sheath 11. The adaptor includes bore 19 for positioning therein proximal member portion 21, i.e., a handle of the insertion member. To fix the relative position of the outer sheath with respect to the insertion member, connector 20 includes first lock member 22 such as a pin extending into adapter bore 19. Second lock member 23 such as a T-shaped slot is formed in the outer surface of the proximal member portion handle to engage and secure pin 22 therein. As a result, surgical tissue morcellator 10 with insertion member 15 fixedly positioned in outer cutting sheath 11 can readily dilate surgical access site 53 and inserted into body cavity 54 of the patient without trauma to the surrounding tissue. To remove insertion member 15 from the outer sheath, the insertion member is rotated relative to outer sheath 11 and withdrawn from outer sheath passage 14.

Figure 2:
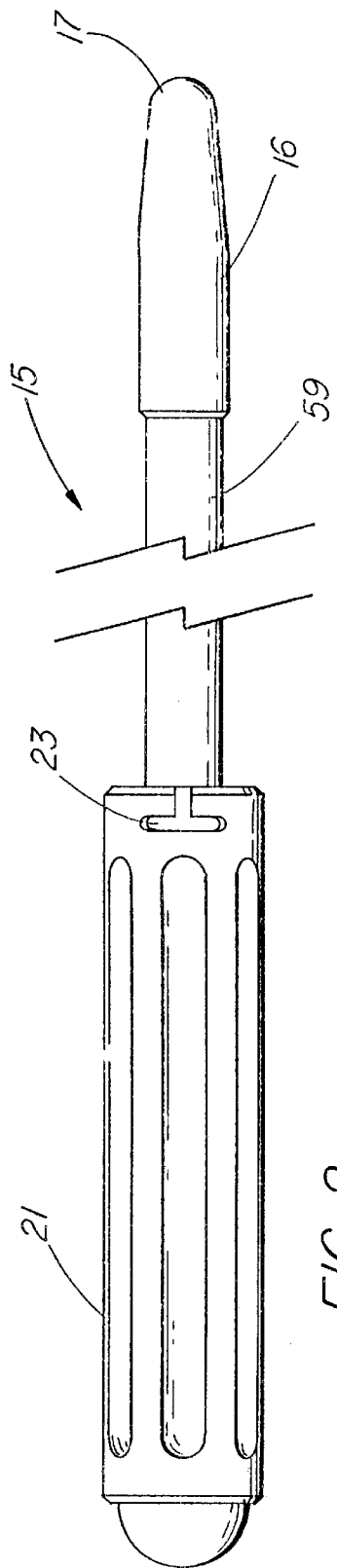
FIG. 2 depicts a side view of an insertion member of the surgical tissue morcellator of FIG. 1.

FIG. 2 depicts a side view of insertion member 15 of the surgical tissue morcellator of FIG. 1. The insertion member includes distal portion 16 with distal insertion end 17, proximal portion 21 that is configured as a handle, and intermediate portion 59 that interconnects the distal and proximal portions. By way of example, distal portion 16 for a 15 mm diameter morcellator is formed from a stainless steel rod that is approximately 50 mm in length and 0.500" in diameter. The distal-most 25 mm of the rod is tapered and rounded to form distal insertion end 17. Proximal portion or handle 21 of the insertion member has a cylindrical shape of hard coated aluminum with an outside diameter of approximately 0.870" and a length of approximately 11.5 cm. The proximal end of the insertion handle is rounded. The remainder of the handle is fluted as depicted to easily grasp and rotate the insertion member and outer cutting sheath. Lock member 23 includes a pair of diametrically opposed T-shaped slots that are formed at the distal end and in the outer surface of the handle. Intermediate portion 59 is a 0.427" diameter stainless steel tube with a 0.010" wall thickness. The overall length of the insertion member is approximately 42 cm. For a 20 mm diameter morcellator, the outer diameter of distal portion 16 is increased to 0.789", and the outside diameter of the intermediate portion stainless steel tube is increased to 0.562" with a 0.028" wall thickness.

Figure 3:
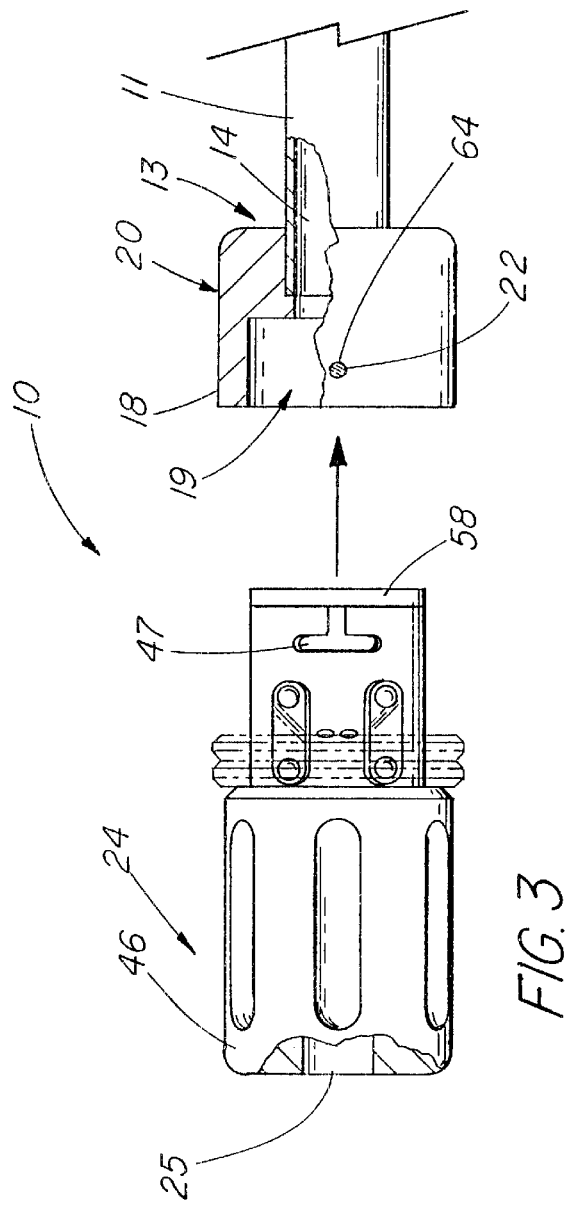
FIG. 3 depicts an enlarged and partially sectioned side view of the tissue morcellator of FIG. 1 and, in particular, the proximal portions thereof.

FIG. 3 depicts an enlarged and partially sectioned side view of tissue morcellator 10 of FIG. 1 and, in particular, proximal portion 13 of outer cutting sheath 11 with connector 20 affixed thereto. As previously suggested, the morcellator also includes removable handle 24 with a main part 46 that is inserted into bore 19 of adaptor 18. Main part 46 is of a generally cylindrically configuration with passage 25 extending longitudinally therethrough. Outer sheath passage 14, adaptor bore 19, and handle passage 25 are coaxially positioned and communicate with each other when handle 24 is positioned in adaptor bore 19. A tissue fixation member is inserted through the handle and outer sheath passages for affixing tissue thereto.

For a 15 mm diameter morcellator, outer cutting sheath 11 is a stainless steel tube having a length of approximately 11.125", an outside diameter of 0.562", and a wall thickness of 0.028". Distal cutting end 12 of the outer sheath is serrated at six equally spaced places around the distal end of the tube with a 0.125" radius cut to a depth of 0.100". The distal cutting end is beveled to a razor sharp edge. Broadband depth marks 60 (FIG. 1) are positioned 5 cm and 10 cm from the distal cutting edge. Narrow-band depth marks 61 are positioned 2.5 cm from the broad-band depth marks.

Adapter 18 of connector 20 is of a cylindrical configuration having a length of approximately 1.000" and an outside diameter of approximately 1.250". Adapter bore 19 is coaxially positioned in the adapter to a depth of 0.500" with a diameter of approximately 0.907". The distal end of the adapter is coaxially bored with a 0.565" diameter to a depth of 0.375" to receive the proximal end of outer cutting sheath tube 11. An epoxy adhesive fixedly joins the adapter and cutting tube at the junction thereof. Two 0.089" diametrically opposed, lock member holes 62 (FIG. 3) are positioned through the wall of the adapter approximately 0.222" from the proximal end of the adapter. Lock members 22 such as two 0.090" diameter bayonet pins approximately 0.250" long are press fitted into lock member holes 62.

Figure 4:
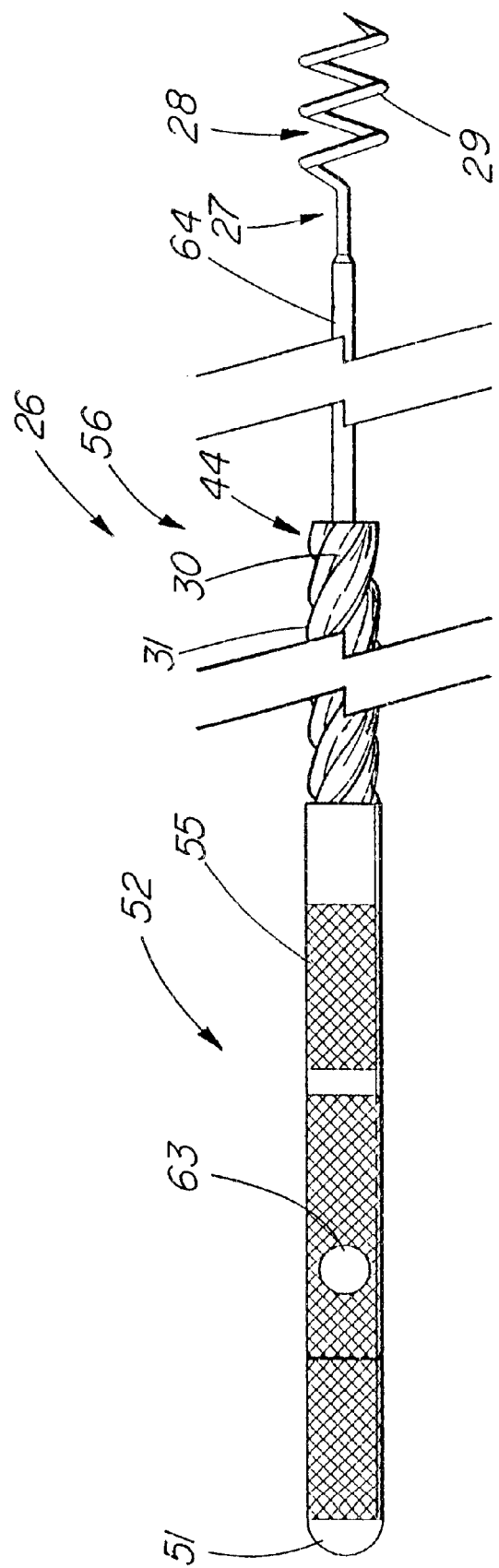
FIG. 4 depicts a side view of a tissue fixation member of the surgical tissue morcellator of the present invention.

FIG. 4 depicts a side view of tissue fixation member 26 of surgical tissue morcellator 10. Tissue fixation member 26 is sized for insertion through outer sheath and handle passages 14 and 25 and includes distal portion 27, which can be extended from the outer sheath passage. Distal portion 27 is, for example, a 0.070" stainless steel rod and has a distal fixation end 28 that is extendable from the distal cutting end of the outer sheath. Distal fixation end 28 includes helical coil or corkscrew 29 that has an outer diameter of approximately 0.375" and a length of 2 cm. The distal end of the helical coil is sharpened for insertion into and fixation of the coil in tissue.

Tissue fixation member 26 also includes a proximal portion such as handle 52 with knurled outer surface 55 and proximal cross member 51, which as depicted is longitudinally threaded into the proximal end of handle. Handle 52 further includes transverse threaded hole 63 for positioning cross member 51 therein and transverse to the handle. The handle consists of a 0.375" stainless steel rod and has an overall length of approximately 9.5 cm with the cross member longitudinally positioned therein. The tissue fixation member further includes intermediate portion 56 with a plurality 44 of helical grooves 30 in external member surface 31 thereof. Plurality 44 of helical grooves 30 includes, preferably, a rolled ⅜" diameter by 1.200" lead, five start, right hand external thread rod approximately 9" long. This threaded rod is commercially available from Precision Screw Thread Corporation of Muskego, Wis. The threaded rod is silver soldered to the handle with a 0.125" stainless steel pin interconnecting them. Multiple starts of external threads provide for more forcible, rapid advancement of the outer cutting sheath with respect to the tissue fixation member while minimizing muscle fatigue of the surgeon during repeated rotation of the outer sheath. The plurality of grooves or multiple external threads also provides for a balanced engagement of the outer sheath with respect to the tissue fixation member. Although the plurality of grooves comprises a five start external thread, it is contemplated that any member of multiple threads can be used depending on torque requirements and speed of engagement. Lastly, tissue fixation member 26 includes second intermediate portion 64 of, for example, a 12-gauge, heavy wall tube interconnecting threaded rod 56 and distal portion 27. As assembled, tissue fixation member 26 is approximately 48 cm in length with the pointed end of helical coil 29 approximately 15.5 cm from the threaded rod of intermediate portion 56.

Figure 5:
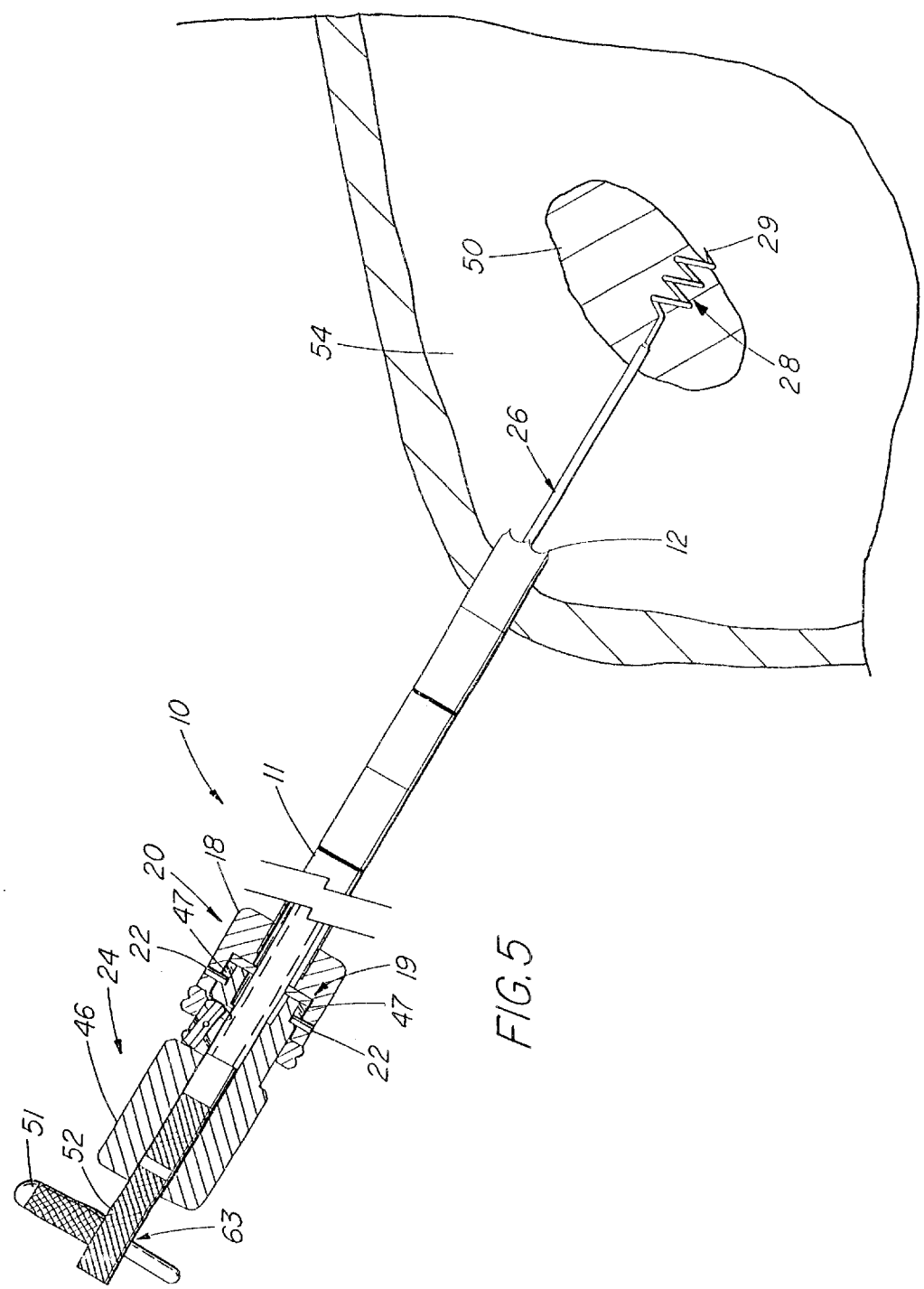
FIG. 5 depicts the surgical tissue morcellator of FIG. 1 in a morcellation configuration and percutaneously positioned in the body cavity of a patient.

FIG. 5 depicts surgical tissue morcellator 10 of FIG. 1 in the morcellation configuration and percutaneously positioned in body cavity 54 of a patient. Tissue fixation member 26 is inserted through outer sheath 11 and handle 24 and affixed in tissue mass 50. Cross member 51 is transversely positioned through hole 63 of handle 52. Cross member 51 allows the physician to apply additional torque for inserting distal fixation end 28 and, in particular, helical coil or corkscrew 29 into tissue mass 50. Morcellator handle 24 is positioned in adaptor bore 19 of connector 20 to fix the relative position of tissue fixation member 26 and outer cutting sheath 11. Similar to insertion member 15, morcellator handle 24 includes lock member 47 such as a T-shaped slot formed in the outer surface of the handle. Two T-shaped slots 47 are diametrically positioned on the outer cylindrical surface of main handle part 46 for respectively positioning therein two other lock members 22 such as press-fitted pins extending radially into adaptor bore 19. The T-shaped slots receive the pins therein as the morcellator handle is positioned in the bore of connector adaptor 18. Morcellator handle 24 is then rotated with respect to the outer cutting sheath to position pins 22 in the top portion of the T-shaped slots. As a result, handle 24 is longitudinally fixedly positioned with respect to outer cutting sheath 11.

Figure 6:
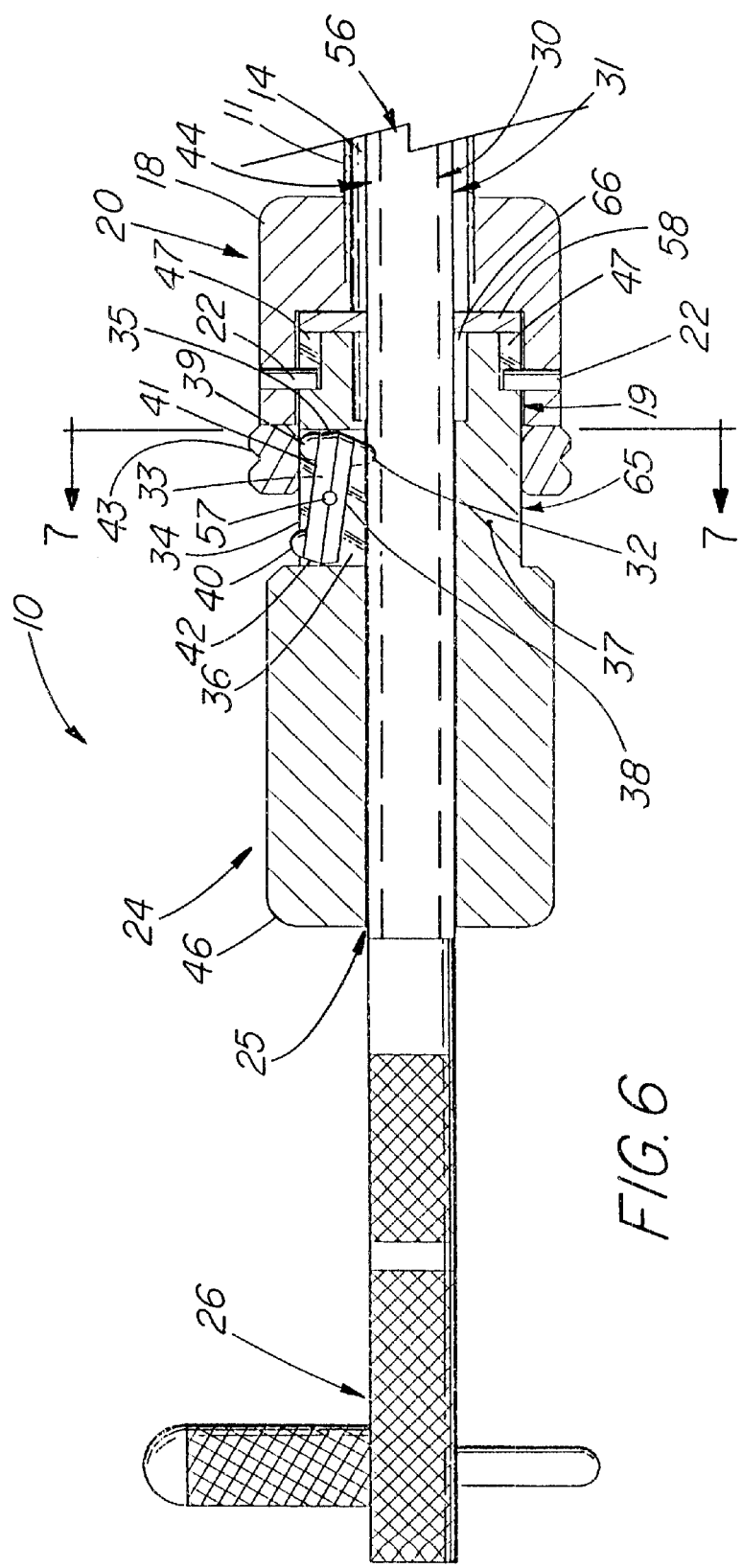
FIG. 6 depicts an enlarged and partially sectioned side view of the surgical tissue morcellator of FIG. 5 and, in particular, the proximal portions thereof.

FIG. 6 depicts an enlarged and partially sectioned side view of surgical tissue morcellator 10 of FIG. 5 and, in particular, the proximal portions thereof. Handle 24 is approximately 2.625" long with neck portion 65 approximately 1.025" long, which is positioned in bore 19 of connector. Main handle part 46 has an outside diameter of approximately 1.250", whereas neck portion 65 has an outside diameter of approximately 0.905". Handle 24, as well as connector adapter 18, consists of, for example, a polycarbonate material. The handle is fixedly positioned in the connector with diametrically positioned lock member pins 22 extending into respective lock members 47 such as T-shaped slots formed in external neck surface 34 of the handle. Handle 24 includes 0.393"diameter handle passage 25, which extends longitudinally therethrough and communicates with connector bore 19 and sheath passage 14. Insufflation gas seal 58 is adhered to the distal end of neck portion 65 and consists of, for example, a 0.125" thick closed-cell silicone material. The distal end of neck portion 65 includes counterbore 66, which has a diameter of approximately 0.500" and a depth of 0.835". The neck counterbore provides relief for seal 58 when tissue fixation member 26 is moved back and forth therethrough. Handle 24 also includes plurality 48 of rocker arm slots 36, which extend longitudinally in neck portion 65 and through wall 37 thereof. Extending from the proximal end of the neck portion, each rocker arm slot is approximately 0.500" long and 0.187" wide with the ends thereof uniformly radiused.

Tissue fixation member 26 of the morcellator is positioned through handle passage 25, connector bore 19, and outer sheath passage 14. Intermediate portion 56 of the tissue fixation member is positioned in handle passage 25 so as to engage plurality 44 of grooves 30 in external member surface 31 thereof.

Figure 7:
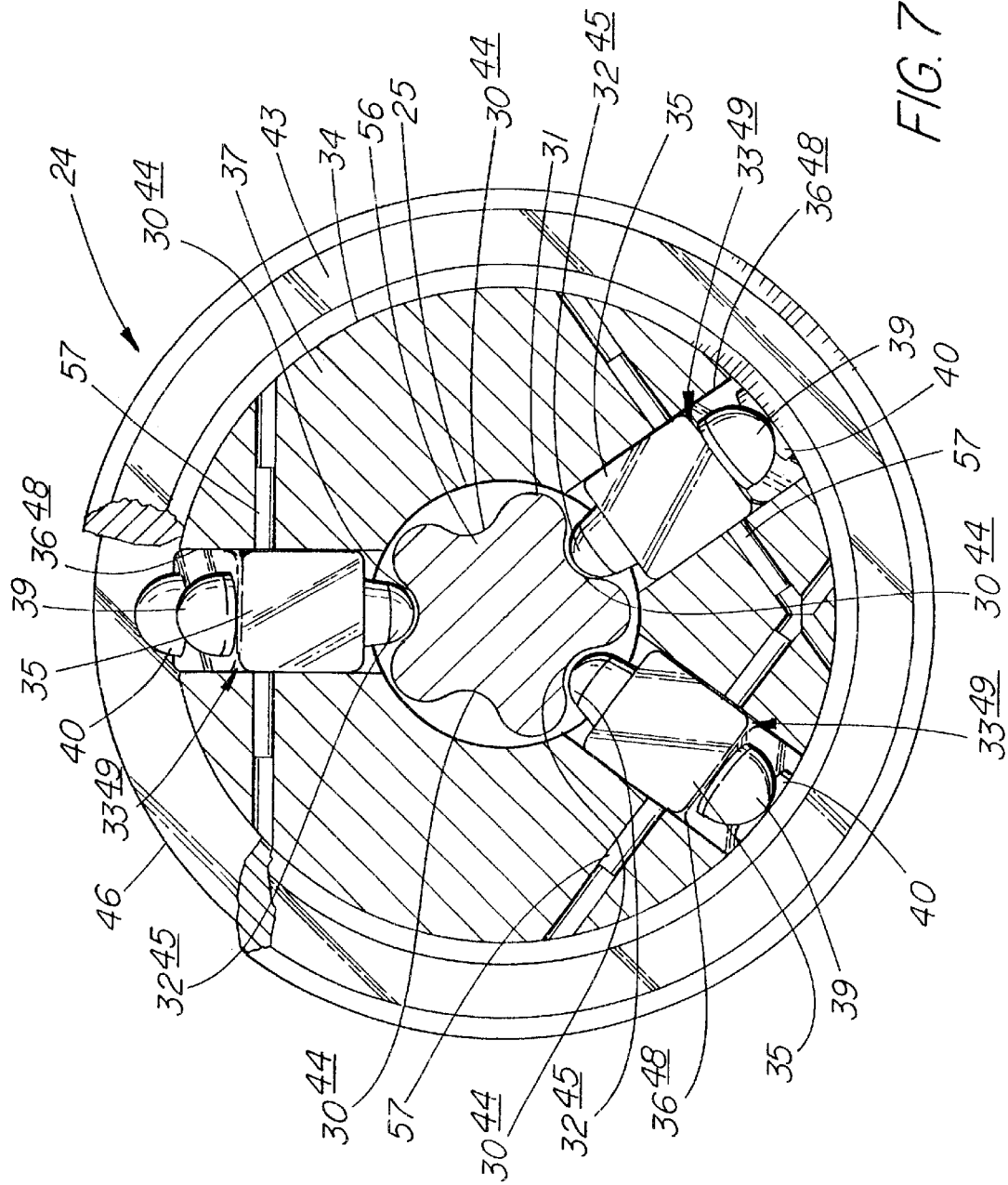
FIG. 7 depicts an enlarged and partially sectioned end view of the handle of the surgical tissue morcellator of FIG. 6 taken along the line 7—7.

FIG. 7 depicts an enlarged and partially sectioned end view of distal neck portion 65 and main handle part 46 of handle 24 of FIG. 6 taken along the line 7—7. This end view depicts plurality 48 of rocker arm slots 36 circumferentially positioned around the distal neck portion and through wall 37 of main handle part 46. Intermediate portion 56 of the tissue fixation member is positioned in handle passage 25 with plurality 44 of helically grooves 30 in external member surface 31. Slot plurality 48 preferably includes three rocker arm slots 36 positioned circumferentially around distal neck portion 65. As a result, two of rocker arm slots 36 are positioned approximately 72 degrees apart with the third rocker arm slot positioned 144 degrees from either of the first two rocker arm slots. Should additional torque be required for advancing the tissue fixation member, two additional rocker arm slots can be formed in distal neck portion 65 with all of the slots being 72 degrees apart from each other.

As depicted in FIGS. 6 and 7, handle 24 also includes plurality 49 of rocker arms 33 pivotally and centrally mounted in respective plurality 48 of rocker arm slots 36 each with a rocker arm pin 57 extending therethrough. A first projection 32 is positioned at first end 35 and on internal side 38 of each rocker arm 33. Each first projection 32 is selectively positionable into handle passage 25 and, particularly, into a corresponding helical groove 30. Second and third projections 39 and 49 are positioned at first and second ends 35 and 42, respectively, on external side 41 of each rocker arm 33. In addition, second and third rocker arm projections 39 and 40 are selectively and externally positionable through external handle surface 34 via retainer ring 43 and rocker arm pins 57.

Handle 24 further includes retainer ring 43 circumferentially positioned around neck portion 65 and, in particular, external neck surface 34. The retainer ring selectively slides longitudinally along external neck surface 34 so as to selectively engage second and third projections 39 and 40 on each of the rocker arms. The retainer ring is also positioned so as to slide on either side of each rocker arm pin 57 and engage either one of second and third projections 39 and 40 extending from the rocker arm slots through external neck surface 34. As depicted in FIG. 6, retainer ring 43 is engaging second projection 39 on each of the rocker arms so as to maintain first projection 32 in handle passage 25, and more particularly, a helical groove of the tissue fixation member. To disengage the tissue fixation member, the retainer ring is slid proximally so as to engage projection 40 at the opposite end of each rocker arm. This engagement pushes each of third projections 40 into its respective rocker arm slot, which causes second projection 39 to extend outwardly from the rocker arm slot and through the external neck surface. As a result, each first projection is withdrawn from handle passage 25 and into its rocker arm slot. When the retainer ring is so positioned, outer cutting sheath 11 and tissue fixation member 26 can be freely slid longitudinally with respect to each other so as to reposition tissue fixation member 26 in the tissue mass.

By way of further example, each rocker arm 36 is approximately 0.580" long, 0.180" wide, and 0.150" high. A rocker arm pin hole is centered in the rocker arm transverse thereto and approximately 0.080" from the top surface. The first projection extends from the bottom surface of the rocker approximately 0.100", whereas the second projection extends 0.083" above the top surface of the rocker arm. The third projection extends approximately 0.062" above the top surface of the rocker arm at the opposite end thereof.

Retainer ring 43 has an outside diameter of approximately 1.400" with an inside diameter of approximately 0.910". The width of the retainer ring is approximately 0.300". The inside edges of the DELRIN material retainer ring are broken as depicted so as to more easily engage the projections.

Figure 8:
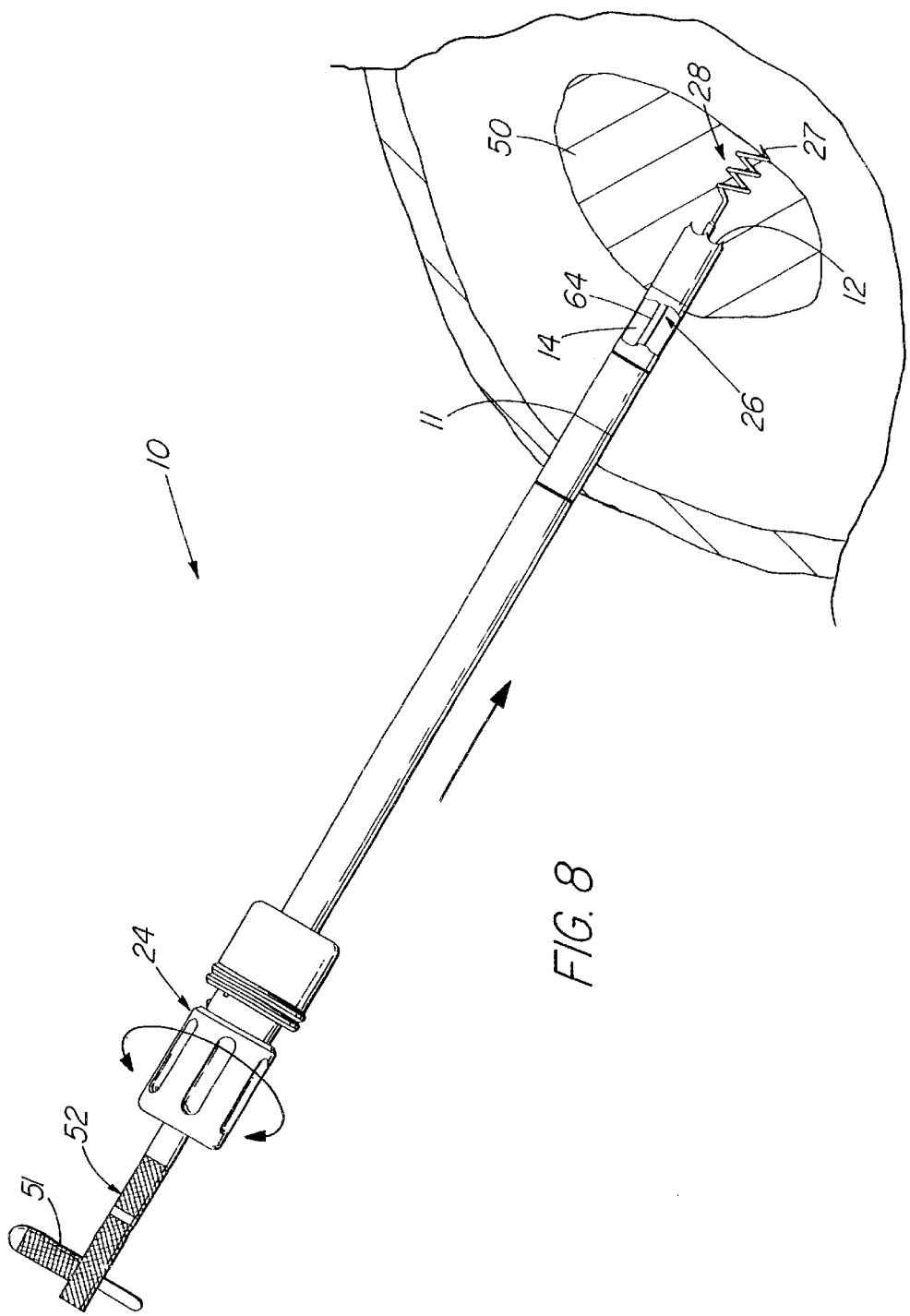
FIG. 8 depicts the surgical tissue morcellator of FIG. 5 with the tissue fixation member affixed to a tissue mass and the outer cutting sheath morcellating the tissue mass.

FIG. 8 depicts surgical tissue morcellator 10 of FIG. 5 with tissue fixation member 26 affixed to tissue mass 50. The physician grasps handle 52 with cross member 51 transversely positioned therethrough and rotates handle 24 with respect to the tissue fixation member. As a result, outer cutting sheath 11 moves longitudinally forward and engages tissue mass 50 with distal cutting end 12 of the outer sheath. The rotational and longitudinal movement of serrated distal cutting end 12 cores tissue mass 50, which is affixed to distal fixation end 28 of tissue fixation member 26. This longitudinal and rotational movement of outer cutting sheath 11 with respect to tissue fixation member 26 is continued until the distal cutting end of the outer sheath is extended through the tissue mass. As a result, a plug of the tissue mass is retained in sheath passage 14 on distal portion 27 and second intermediate portion 64 of the tissue fixation member.

Figure 9:
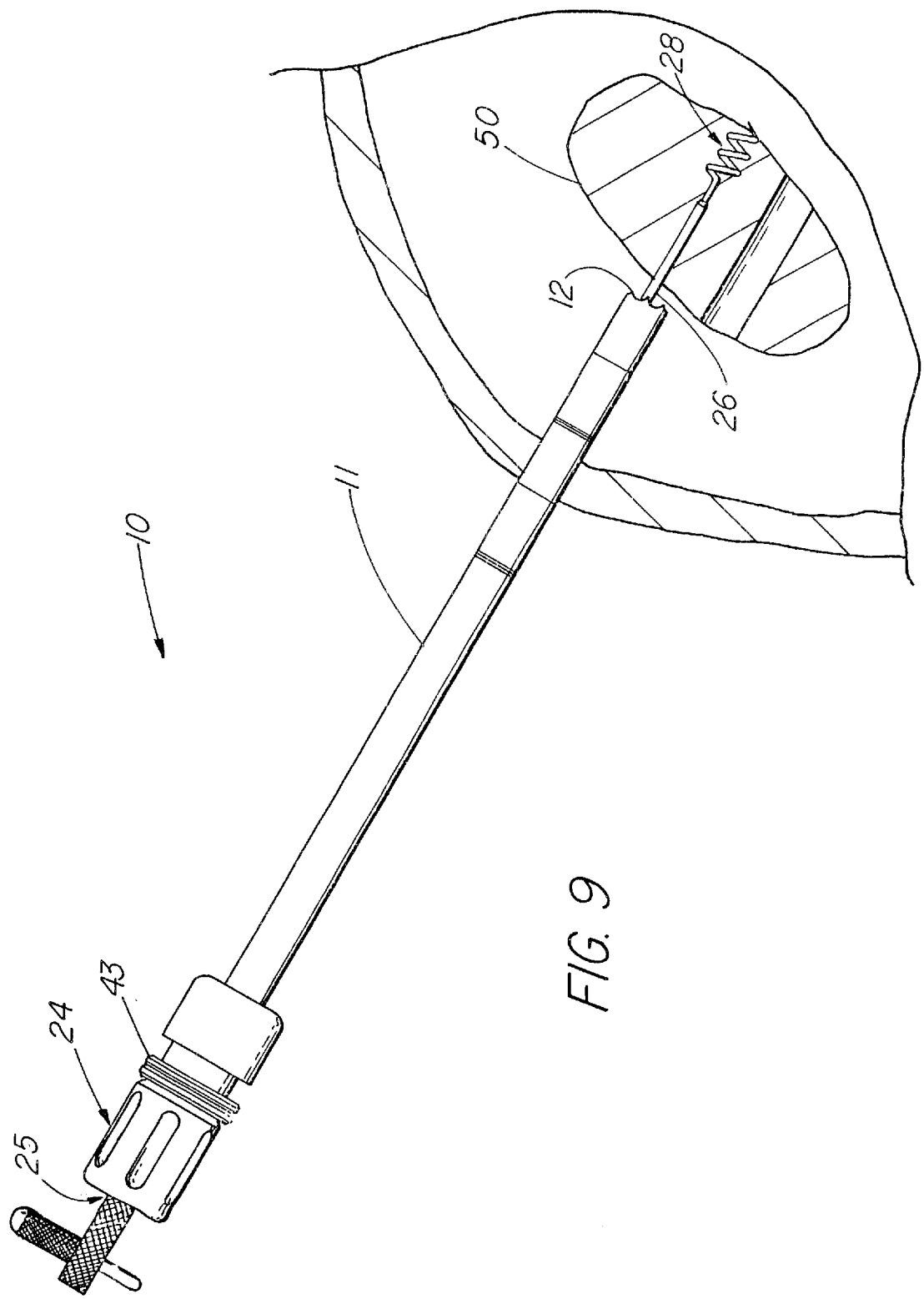
FIG. 9 depicts the surgical tissue morcellator of FIG. 5 being repositioned to morcellate another core of the tissue mass.

FIG. 9 depicts surgical morcellator 10 of FIG. 5 with distal fixation end 28 of tissue fixation member 26 being extended from distal cutting end 12 of outer sheath 11 and repositioned to morcellate another plug of tissue mass. Retainer ring 43 of handle 24 has been moved backwards so as to retract the rocker arm projections from handle passage 25 and the plurality of helical grooves from tissue fixation member 26. In this repositioning procedure, the physician extends the distal fixation end of member 26 from the outer sheath for another engagement with tissue mass 50. When the distal end of the tissue fixation member has been reanchored in the tissue mass, the retainer ring of the handle is slid forward extending the first rocker arm projections into the helical grooves of the tissue fixation member. When the first rocker arm projections engage the helical grooves, the physician repeats the procedure of rotating handle 24 so that distal end 12 again engages and cores another plug of tissue mass 50. This procedure is repeated until tissue mass 50 has been debulked. Any small amounts of tissue remaining after the morcellation of tissue mass 50 can be aspirated or removed through outer cutting sheath 11. Alternatively, the fibroid tissue mass can be first positioned in a surgical tissue bag, which is commercially available from Cook Urological Inc., Spencer, Ind., and morcellated therein.

It is to be understood that the above-described surgical tissue morcellator is merely an illustrative embodiment of the principles of this invention and that other surgical tissue morcellators may be devised by those skilled in the art without departing from the spirit and the scope of this invention. It is contemplated that the morcellator handle can include additional rocker arm slots extending through the wall thereof. Additional rocker arms can be inserted so as to provide additional engagement points for the tissue fixation member in the situation where even more force is required for coring extremely tough and fibrous tissue masses. These additional rocker arms are also engaged by the same retainer ring. More or less helical grooves or external threads can be formed in the intermediate portion of the tissue fixation member to accommodate any number of rocker arm engagement points and to alter or vary the relative longitudinal movement of the outer cutting sheath with respect to the tissue fixation member during one rotation of the outer cutting sheath. It is further contemplated that the distal end of the tissue fixation member can comprise any grasping apparatus such as a hook, a spike, fingers, or forcep jaws.

What is claimed is:

1. A surgical tissue morcellator assembly (10) comprising:
an outer sheath (11) having a distal cutting end (12), a proximal sheath portion (13), and a sheath passage (14) extending longitudinally therein;
an insertion member (15) having a distal portion (16) which can be inserted through said sheath passage, said distal portion including a distal insertion end (17) that is atraumatic to tissue (50) and extendable from said distal cutting end of said outer sheath; and a connector (20) disposed on at least one of said outer sheath and said insertion member and configured to position said insertion member relative to said outer sheath.

2. The surgical tissue morcellator assembly of claim 1 wherein said insertion member includes a proximal member portion (21) and wherein said connector includes an adapter (18) connected to said proximal sheath portion and configured to join said proximal sheath portion and said proximal member portion.

3. The surgical tissue morcellator assembly of claim 2 wherein said adapter includes a bore (19) therein communicating with said sheath passage and configured to receive said proximal member portion therein.

4. The surgical tissue morcellator assembly of claim 3 wherein said connector includes a first lock member (22) extending into said bore of said adapter and wherein said proximal member portion includes a second lock member (23) disposed therein to receive said first lock member.

5. The surgical tissue morcellator assembly of claim 1 further comprising a handle (24) having a handle passage (25) communicating with said sheath passage when said handle is positioned relative to said outer sheath and wherein said connector is also configured to position said handle relative to said outer sheath.

6. The surgical tissue morcellator assembly of claim 5 further comprising a tissue fixation member (26) at least a portion (27) of which can be inserted through said sheath and said handle passages and having a distal fixation end (28) that can be extended from said distal cutting end of said outer sheath, said distal fixation end of said tissue fixation member having a part (29) fixable in tissue.

7. The surgical tissue morcellator assembly of claim 6 wherein said tissue fixation member includes a helical groove (30) in an external member surface (31) thereof and wherein said handle includes a projection (32) selectively extending into said handle passage and said helical groove when said helical groove is positioned in said handle passage.

8. The surgical tissue morcellator assembly of claim 7 wherein said handle includes a rocker arm (33) that extends between an external handle surface (34) and said handle passage (25) and wherein said projection is positioned about a first rocker arm end (35) extending into said handle passage.

9. The surgical tissue morcellator assembly of claim 8 wherein said rocker arm is pivotally mounted in a slot (36) extending through a wall (37) of said handle; wherein said projection is mounted on a first side (38) of said rocker arm at said first rocker arm end; wherein a second and a third projection (39, 40) are positioned on a second side (41) opposite said first side and at said first and a second rocker arm end (42), respectively; and wherein said handle further comprises a retainer (43) that selectively moves to engage said second and third projections on said second side of said rocker arm.

10. The surgical tissue morcellator assembly of claim 7 wherein said tissue fixation member includes a plurality (44) of said helical groove and wherein said handle includes a plurality (45) of said projection selectively extending into said plurality of said helical groove.

11. A surgical tissue morcellator assembly (10) comprising:
an outer sheath (11) having a distal cutting end (12), a proximal sheath portion (13), and a sheath passage (14) extending longitudinally therein; and
a handle (24) removably connected to said proximal sheath portion and having a handle passage (25) extending longitudinally therethrough and communicating with said sheath passage, said handle also having a slot (36) extending through a wall (37) thereof and a rocker arm (33) pivotally mounted in said slot and communicating with said handle passage and an external handle surface (34), said rocker arm on a first side (38) and at a first rocker arm end (35) having a first projection (32) communicating with and extendable into said handle passage, said rocker arm having a second side (41) opposite said first side and communicating with said external handle surface, said handle further comprising a retainer (43) disposed about said rocker arm and movable to engage selectively said first and a second end (42), whereby longitudinal and rotational movement of said outer sheath causes said distal cutting end to rotate and core tissue affixed to a tissue fixation member (26) positioned in said handle and said sheath passages and engaging said first projection on said first rocker arm end.

12. The surgical tissue morcellator assembly of claim 11 wherein said morcellator further comprises an adapter (18) disposed on said proximal sheath portion and having a bore (19) therein communicating with said handle and said sheath passages, said handle being configured for positioning in said bore of said adaptor.

13. The surgical tissue morcellator assembly of claim 12 wherein said adapter includes a first lock member (22) extending into said bore and wherein said handle includes a second lock member (47) disposed therein to receive said first lock member.

14. The surgical tissue morcellator assembly of claim 11 wherein said handle further comprises a plurality (49) of said rocker arm (33) pivotally mounted in a respective plurality (48) of said slot (37).

15. The surgical tissue morcellator of claim 14 further comprising a tissue fixation member (26) at least a portion (27) of which can be inserted through said sheath and said handle passages and having a distal fixation end (28) which can be extended from said distal cutting end of said outer sheath, said distal fixation end having a part (29) fixable in tissue.

16. The surgical tissue morcellator assembly of claim 15 wherein said tissue fixation member includes a plurality (44) of said helical groove and wherein said plurality of said rocker arm includes a plurality (45) of said projection selectively extending into said plurality of said helical groove.

17. The surgical tissue morcellator assembly of claim 11 wherein said surgical tissue morcellator further comprises a tissue fixation member (26) at least a portion (27) of which can be inserted through said sheath and said handle passages and having a distal fixation end (28) which can be extended from said distal cutting end of said outer sheath, said distal fixation end having a part (29) fixable in tissue; wherein said tissue fixation member includes a helical groove (30) in an external member surface (31) thereof; and wherein said handle includes a projection (32) selectively extending into said handle passage and said helical groove when said helical groove is positioned in said handle passage.

18. The surgical tissue morcellator assembly of claim 11 further comprising an insertion member (15) at least a portion (16) of which can be inserted through said sheath passage and having a distal insertion end (17) which is atraumatic to tissue (50) and can be extended from said distal cutting end of said outer sheath when said at least said portion of said insertion member is inserted through said sheath passage.

19. The surgical tissue morcellator assembly of claim 17 wherein said surgical tissue morcellator further comprises a connector (20) disposed on said proximal sheath portion and configured to position said insertion member relative to said outer sheath.

20. A surgical tissue morcellator assembly (10) comprising:

an outer sheath (11) having a distal cutting end (12), a proximal sheath portion (13), and a sheath passage (14) extending longitudinally therein;

a handle (24) removably connected to said proximal sheath portion and having a handle passage (25) extending longitudinally therethrough and communicating with said sheath passage, said handle also having a plurality of slots (48) extending through a wall (37) thereof and a respective plurality of rocker arms (49) pivotally mounted in said plurality of slots and communicating with said handle passage and an external handle surface (34), each of said plurality of rocker arms on a first side (38) and at a first end (35) having a first projection (32) communicating with and extendable into said handle passage, each of said plurality of rocker arms on a second side (41) opposite the first side and at the first and a second end having a second (39) and a third projection (40), respectively, said handle further having a retainer (43) positioned around said plurality of rocker arms and slidable to engage selectively the second and third projections on each of said plurality of rocker arms;

an adapter disposed on said proximal sheath portion and having a bore (19) therein communicating with said handle and said sheath passages, said bore being configured to position said handle therein, said adapter including a pin (22) extending radially into said bore;

a tissue fixation member (26) at least a portion (27) of which can be inserted through said sheath and said handle passages and having a distal fixation end (28) which can be extended from said distal cutting end of said outer sheath, said distal fixation end of said tissue fixation member having a part (29) fixable in tissue;

wherein said tissue fixation member includes a plurality of helical grooves (44) in an external surface (31) thereof;

wherein the first projections of said handle selectively extend into said plurality of said helical grooves; and wherein said tissue fixation member includes a cross member (51) transversely positionable on said tissue fixation member about a proximal end (52) thereof.

* * * * *